(12) United States Patent
Prewett

(10) Patent No.: US 7,645,475 B2
(45) Date of Patent: Jan. 12, 2010

(54) DEVICES HAVING A TEXTURED SURFACE

(75) Inventor: Donovan D. Prewett, Irving, TX (US)

(73) Assignee: Mentor Corporation, Santa Barbara, CA (US)

( * ) Notice: Subject to any disclaimer, the term of this patent is extended or adjusted under 35 U.S.C. 154(b) by 727 days.

(21) Appl. No.: 11/071,857

(22) Filed: Mar. 3, 2005

(65) Prior Publication Data

US 2005/0216094 A1 Sep. 29, 2005

Related U.S. Application Data

(60) Provisional application No. 60/549,651, filed on Mar. 3, 2004.

(51) Int. Cl.
*A61F 2/12* (2006.01)
*B05D 1/12* (2006.01)
*B05D 1/38* (2006.01)

(52) U.S. Cl. .................. 427/2.24; 427/2.1; 427/180; 427/202; 427/203; 427/204; 623/7; 623/8

(58) Field of Classification Search ......... 427/202–204, 427/2.1, 2.24; 623/7, 8
See application file for complete search history.

(56) References Cited

U.S. PATENT DOCUMENTS

| | | | | |
|---|---|---|---|---|
| 2,925,831 A * | 2/1960 | Welty et al. | ........... | 138/141 |
| 4,455,691 A | 6/1984 | Redinger et al. | | |
| 4,955,909 A | 9/1990 | Ersek et al. | ........... | 623/11 |
| 4,960,425 A | 10/1990 | Yan et al. | ........... | 623/8 |
| 4,963,150 A | 10/1990 | Brauman | ........... | 623/8 |
| 5,002,572 A | 3/1991 | Picha | ........... | 623/11 |
| 5,011,494 A | 4/1991 | Von Recum et al. | ........... | 623/11 |
| 5,022,942 A | 6/1991 | Yan et al. | ........... | 156/219 |
| 5,158,571 A | 10/1992 | Picha | ........... | 623/11 |
| 5,207,709 A | 5/1993 | Picha | ........... | 623/11 |
| 5,219,361 A | 6/1993 | Von Recum et al. | ........... | 623/11 |
| 5,236,453 A | 8/1993 | Picha | ........... | 623/8 |
| 5,296,069 A | 3/1994 | Robert | ........... | 156/242 |
| 5,354,338 A * | 10/1994 | Ledergerber | ........... | 623/8 |
| 5,525,275 A | 6/1996 | Iverson et al. | ........... | 264/28 |
| 5,545,220 A | 8/1996 | Andrews et al. | ........... | 623/8 |
| RE35,391 E | 12/1996 | Brauman | ........... | 623/8 |
| 5,658,330 A | 8/1997 | Carlisle et al. | | |
| 5,674,285 A * | 10/1997 | Quaid | ........... | 623/8 |
| 5,935,164 A | 8/1999 | Iverson | ........... | 623/8 |
| 5,961,552 A * | 10/1999 | Iversen et al. | ........... | 623/8 |
| 5,964,803 A | 10/1999 | Iverson et al. | ........... | 623/8 |
| 5,965,076 A | 10/1999 | Banks et al. | ........... | 264/219 |
| 6,146,418 A | 11/2000 | Berman | ........... | 623/8 |
| 6,179,872 B1 | 1/2001 | Bell et al. | ........... | 623/11.11 |
| 6,183,514 B1 | 2/2001 | Becker | ........... | 623/8 |

(Continued)

FOREIGN PATENT DOCUMENTS

AU 15523/88 5/1988

(Continued)

*Primary Examiner*—Timothy H Meeks
*Assistant Examiner*—Cachet I Sellman

(57) ABSTRACT

A method for forming a randomly textured surface on an implantable device such as soft tissue prosthesis. The textured surface has numerous cavities, interstices and passageways or tunnels and is thus referred to as a microporous surface texture. The surface is formed by two or more applications of polymeric particles and a polymeric dispersion.

44 Claims, 3 Drawing Sheets

U.S. PATENT DOCUMENTS

| | | |
|---|---|---|
| 6,228,116 B1 | 5/2001 | Ledergerber .................... 623/8 |
| 6,255,360 B1 | 7/2001 | Domschke et al. ............. 521/64 |
| 6,306,424 B1 | 10/2001 | Vyakarnam et al. ......... 424/426 |
| 6,605,116 B2 | 8/2003 | Falcon et al. .................... 623/8 |
| 6,673,404 B1 | 1/2004 | Tony et al. |
| 6,692,527 B1 | 2/2004 | Bellin et al. ..................... 623/8 |
| 6,743,254 B2 | 6/2004 | Guest et al. ...................... 623/8 |
| 2001/0010024 A1 | 7/2001 | Ledergerber ............. 623/23.74 |
| 2001/0041936 A1 | 11/2001 | Corbitt, Jr. et al. .............. 623/8 |
| 2002/0038147 A1 | 3/2002 | Miller, III ....................... 623/8 |
| 2003/0149481 A1 | 8/2003 | Guest et al. ..................... 623/8 |
| 2003/0208269 A1 | 11/2003 | Eaton et al. ..................... 623/7 |
| 2004/0127985 A1 | 7/2004 | Bellin et al. .................... 623/8 |
| 2005/0004526 A1 | 1/2005 | Reinemann et al. ......... 604/175 |

FOREIGN PATENT DOCUMENTS

AU              617667            5/1991

* cited by examiner

DEVICES HAVING A TEXTURED SURFACE

RELATED APPLICATION INFORMATION

This application claims priority to U.S. provisional application Ser. No. 60/549,651, filed Mar. 3, 2004, the contents of which is hereby incorporated by reference.

TECHNICAL FIELD

This application relates to devices implantable in the human body such as prostheses and catheters, pacemakers, implantable sensors and other implantable devices that are desirably anchored to tissue within the body.

BACKGROUND

Implantable prostheses are commonly used to replace or augment body tissue. For example, in the case of the female breast, it sometimes necessary to remove some or all of the mammary gland and surrounding tissue in order to treat breast cancer. This surgery leaves a void that can be filled with an implantable prosthesis. The prosthesis serves to support surrounding tissue and to maintain the appearance of the body. The restoration of the normal appearance of the body has a beneficial psychological effect on post-operative patients, reducing the shock and depression that can often follows extensive surgical procedures. Implantable mammary prostheses are also used more generally for enlargement of the breast. Implantable mammary prostheses are commonly formed of a silicone polymer shell and are filled with saline or some other fluid or gel.

After implantation, collagenous scar tissue generally forms around the implant. This process is commonly referred to as encapsulation. The nature and degree of scar tissue formation is thought to depend on a variety of factors, including: location of the implant, the degree of relative movement between the implant and surrounding tissue, implant size, implant shape, and the surface texture of the implant. In some circumstances, the scar tissue can contract in a process referred to as capsular contracture. This can cause undesirable hardening of the tissue surrounding the implant and can distort the shape of the implant.

For a variety of reasons it can be desirable for an implant such as a soft tissue prosthesis or an implantable sensor to become anchored to surrounding tissue. For example, anchoring can reduce large scale displacement of the implant from the desired location and can reduce relative movement between the implant and surrounding tissue.

Various methods for providing a textured surface to an implantable prosthesis have been described.

Iverson et al. (U.S. Pat. No. 5,964,803 and U.S. Pat. No. 5,525,275) describe an implantable prosthesis having a textured surface formed by depositing a cured polymeric particles on an uncured, tacky surface. This surface on which the particles are deposited is cured and a layer of "uncured elastomeric material" is applied. The entire surface is then cured to create a surface "characterized by a random distribution of peaks separated by valleys." According to Iverson et al., the "the peaks and valleys are separated by gradual contoured slopes with a smooth transition between the peaks and valleys". Also according to Iverson et al., the "transitions are substantially free of indentations and interstices which may trap body fluids."

Ersek et al. (U.S. Pat. No. 4,955,909) describe a molding process that is said to create "a net-like surface grid structure including pillars extending outwardly from a base plane . . . along with indentations or pores being formed in the outer end projecting surfaces of pillars."

Robert (U.S. Pat. No. 5,296,069) describes creating a textured surface on an implant by pressing a foam sheet against an unvulvanized silicone sheet.

Yan et al. (U.S. Pat. No. 4,960,425) describe implants having a textured surface that "consists of a plurality of substantially microscopic peaks and valleys substantially free of pores or interstices" One of the methods for creating such a surface entails coating a textured mandrel with silicone.

Yan et al. (U.S. Pat. No. 5,022,942) describe implants having a textured surface "formed of non-absorbent material substantially free of pores and interstices". The surface can be created in a number of ways, including by applying a formable, biocompatible material over at least a portion of the exterior surface of the shell and disposing a texturizing means over the deformable material to imprint a texture on the deformable material.

SUMMARY

Methods for providing a textured surface on a device designed for implantation into the body of a patient, e.g., a prosthesis or catheter or other implantable device are described herein. Silicone and other elastomeric polymers can be used to create the textured surface on the device. The device itself can be formed in whole or in part from an elastomeric polymer or it can be formed in whole or in part of some other material (e.g., metal or plastic) and the textured surface can be formed on the device by applying an elastomeric material to all or a portion of the device. The textured surface is irregular and has numerous cavities and interstices. Thus, in some embodiments, the textured surface has cavities and interstices into which tissue can grow after the device has been implanted in a patient. Some of these cavities can be wider at their base than near their top and others can be narrower at their base than near their top. In some embodiments, the textured surface can also have passageways or short tunnels through which tissue can grow when the device is implanted in a patient so that portions of the surface texture become embedded in tissue.

The textured surface is created by applying solid particles formed of a polymeric material (e.g., particles of silicone) to a surface (e.g., uncured, partially cured or fully cured silicone) and then coating the particles with a liquid polymer dispersion (e.g., a silicone dispersion). Any suitable polymer, e.g., silicone, polyurethane, modified polyurethane, or silicone polyurethane, can be used for the particles and for the dispersion. The particles and the dispersion can be the same polymer or different polymers. In general, the textured surface is created by applying two or more layers of particles stacked on top of each other in a non-uniform fashion. Each of the two more layers of particles is separately coated with a dispersion of silicone or some other polymer. Within each layer of particles the particles can be randomly stacked such that some particles rest on other particles. In this case the layer of particles is at least two particles thick in most regions. In other cases, the particles in a given layer of particles are not stacked. In this case, the layer of particles is only one particle thick in most regions. A layer of particles can be coated with a liquid polymer dispersion, one, two, three or more times. Where a layer of particles is coated with a polymer dispersion two or more times, each coating layer can be fully polymerized, partially polymerized or not polymerized before the next coating layer is applied.

Because the particles are coated with a polymer dispersion after they are applied to the surface of the device, the particles are firmly attached to the device. Moreover, while the textured surface is irregular, it is relatively free of sharp edges because the polymer dispersion applied to the particles coats the particles and creates somewhat gently rounded edges. The textured surface includes cavities, interstices and, in some cases, tunnels or passageways. The cavities, interstices and tunnels or passageways permit tissue ingrowth after the device has been implanted in a patient. Accordingly, the textured surface is expected to allow for better adhesion between the implanted device and surrounding tissue than can be achieved with a smooth surface. Moreover, in the case of a prosthesis such as a mammary prosthesis, the textured surface has the potential to reduce capsular contraction and increase vascularization compared to a smooth surface.

A textured surface on a workpiece can be created by a method that includes: a) providing a workpiece having a surface; b) applying particles of a solid polymeric material to at least a portion of the surface to create a particle covered portion of the surface; c) applying at least one coat of a polymer dispersion to at least the particle covered portion of the surface to create a coated surface; d) applying particles of a solid polymeric material to at least a portion of coated surface; and e) applying at least one coat of a polymer dispersion to at least the particle covered portion of the coated surface.

In some instances: steps d) and e) are repeated such that there are alternating multiple applications of particles of a solid polymeric material and multiple applications of polymer dispersion (e.g., three, four, five, six or more applications of each); the solid polymeric particles are silicone particles (e.g., high temperature vulcanization (HTV) or room temperature vulcanization (RTV) silicone); the polymer dispersion is a silicone dispersion (e.g., HTV or RTV silicone); the particles of a solid polymeric material are applied to the entire coated surface; the particles of a solid polymeric material are applied to only a portion of the coated surface; and the silicone dispersion applied to a layer of silicone particles is at least partially cured before application of a subsequent layer of silicone particles.

In other instances: the workpiece is formed at least in part of silicone; the surface to which the particles are applied (e.g., the surface to which the first layer of particles is applied) is uncured or partially cured silicone; the workpiece is the shell of an implantable prosthesis (e.g., a mammary prosthesis) or tissue expander; the average size of the particles used in the first application of particles differs from the average size of the particles used in the second application of particles; the average size of the particles used in at least one of the multiple applications of particles differs from the average size of the particles used in at least one other of the multiple applications of particles; the average size of the particles in each of the multiple applications of particles differs in average size from the average size of the particles used in each of the other multiple applications of particles; the average size of the particles in a given layer is greater than the average size of the particles in the subsequently applied layer or layers; and the average size of the particles in a given layer is less than the average size of the particles in the subsequently applied layer or layers.

In other instances: the polymer dispersion is applied by spraying; the polymer dispersion is applied by dipping; the particles of polymeric material are applied by spraying the particles; and the particles of polymeric material are applied by dipping the workpiece into particles, e.g., a fluidized bed of particles; the particles are suspended in a silicone dispersion; the silicone dispersion used to coat a layer of particles contains between 6% and 15% solids, between 8% and 13% solids, or between 9% and 11% solids; and the solvent in the silicone dispersion is xylene.

An implant shell having a textured surface can be formed by a method comprising: a) providing a implant shell formed of a polymeric material (e.g., a shell formed of uncured, partially cured or fully cured silicone); b) applying particles of a solid polymeric material to at least a portion of at least one surface of the shell to create a particle covered portion of the surface; c) applying a polymer dispersion to at least the particle covered portion of the surface to create a coated surface; d) applying particles of a solid polymeric material to at least a portion of coated surface; and e) applying a polymer dispersion to at least the particle covered portion of the coated surface.

Useful products include an implant shell (e.g., a shell for a mammary prosthesis) produced by a method comprising: a) providing a implant shell formed of a polymeric material (e.g., a shell formed of uncured, partially cured or fully cured silicone); b) applying particles of a solid polymeric material to at least a portion of at least one surface of the shell to create a particle covered portion of the surface; c) applying a polymer dispersion to at least the particle covered portion of the surface to create a coated surface; d) applying particles of a solid polymeric material to at least a portion of coated surface; and e) applying a polymer dispersion to at least the particle covered portion of the coated surface.

In certain instances: the implant shell is produced by a method that includes: repeating steps d) and e) such that there are alternating multiple applications of particles of a solid polymeric material and multiple applications of polymer dispersion (e.g., steps d) and e) each occur at least 3, 4, 5, 6 or more times); the use of solid polymeric particles that are silicone particles; the use of a polymer dispersion that is a silicone dispersion; and at least partially curing the silicone dispersion applied to a layer of particles before the application of a subsequent layer of silicone particles.

A soft tissue prosthesis can be formed by a method comprising: a) providing a shell formed of a polymeric material; b) applying particles of a solid polymeric material to at least a portion of at least one surface of the shell to create a particle covered portion of the surface; c) applying a polymer dispersion to at least the particle covered portion of the surface to create a coated surface; d) applying particles of a solid polymeric material to at least a portion of coated surface; e) applying a polymer dispersion to at least the particle covered portion of the coated surface; and f) sealing the shell and providing the shell with a filling port. The invention also features a soft tissue prosthesis (e.g., a mammary prosthesis) produced by the forgoing method.

Useful products include a soft tissue prosthesis having a shell formed of a polymeric material wherein at least a textured portion of the surface of the shell bears particles of silicone that are coated with a layer of silicone, wherein the textured portion of the surface is characterized by cavities at least some of which are connected beneath the surface and wherein the particles of silicone are stacked one upon another. In certain instances the textured portion of the surface bears at least two layers of particles of polymeric material and each layer of particles is coated with a layer of polymer. In some instances, some or all of the at least two layers of particles have particles stacked one upon another such that the layer of particles is at least two particles thick.

Useful products also include a shell of soft tissue prosthesis formed of a polymeric material wherein at least a textured portion of the surface of the shell bears particles of silicone that are coated with a layer of silicone, wherein the textured portion of the surface is characterized by cavities at least some of which are connected beneath the surface and wherein the particles of silicone are stacked one upon another. In certain instances the textured portion of the surface bears at least two layers of particles of polymeric material and each layer of particles in coated with a layer of polymer. In some instances, some or all of the at least two layers of particles have particles stacked one upon another such that the layer of particles is at least two particles thick.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Described below are methods for creating a randomly textured surface on a device, e.g., a device implantable in a human body such as a soft tissue prosthesis, catheter, pacemaker, implantable sensor or other device that is desirably anchored to tissue within the body. The randomly textured surface has numerous cavities, interstices and, in some instances, passageways or tunnels. In case of a body implant, the cavities and interstices can facilitate the ingrowth of tissue and the anchoring of the device to tissue within the body.

Figure 1:
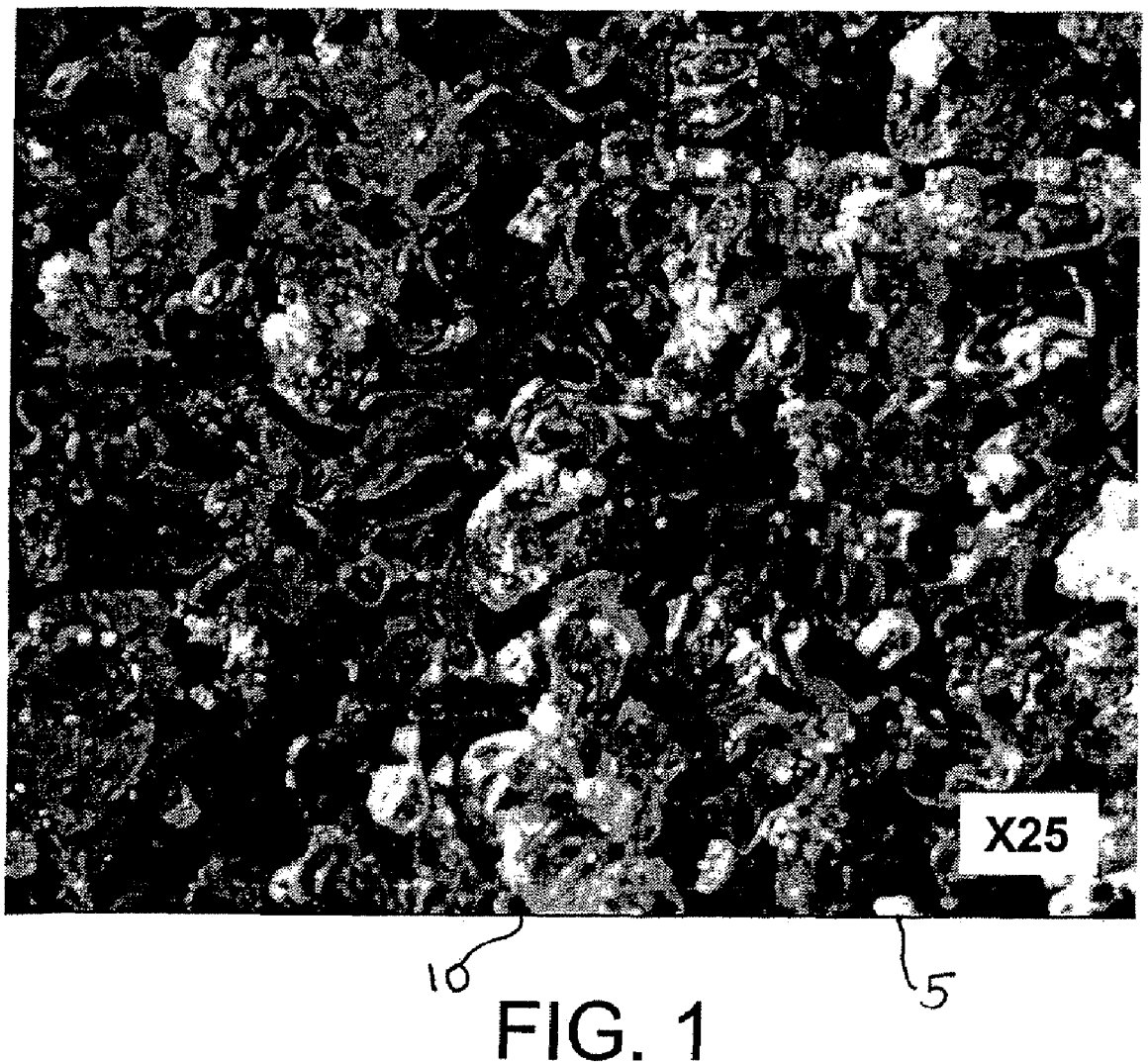
FIG. 1 is photograph of the surface of a sheet of silicone having a textured surface applied according to one variation of a method described herein.

FIG. 1 is a photograph of the surface of a sheet of silicone having a surface texture applied according one variation of a method described herein. Encapsulated particles 5 create a random surface. Numerous pores 10 are apparent.

Figure 2A:
FIG. 2A is a photograph of a cross-section of a sheet of silicone having a textured surface applied according to one variation of a method described herein.

FIG. 2A is a photograph of a cross-section of a sheet of silicone having a textured surface applied according to one variation of a method described herein. The surface to which the first layer of particles was applied is indicated by an arrow.

Figure 2B:
FIG. 2B is a photograph of a cross-section of a sheet of silicone having a textured surface applied according to one variation of a method described herein. Some of the applied particles are circled.

FIG. 2B is a photograph of a cross-section of a sheet of silicone having a textured surface applied according to one variation of a method described herein. Some of the applied particles are circled.

Figure 3:
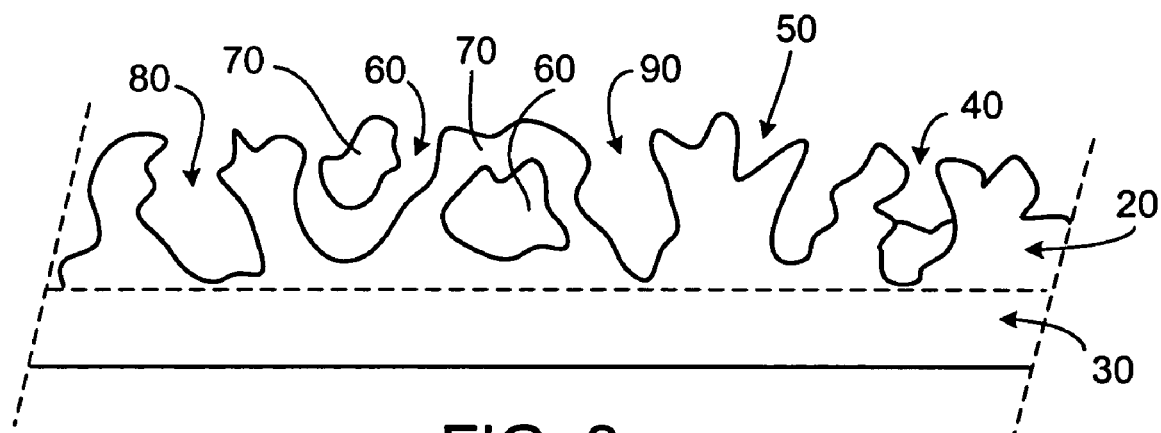
FIG. 3 is schematic drawing of a cross-section of a sheet of silicone having a textured surface applied according to one variation of a method described herein. Individual particles are not shown.

FIG. 3 is a schematic drawing of a cross-sectional view of a portion of the shell of a mammary implant having a textured surface applied according to one variation of a method described herein. The textured surface 20 is applied to one face of the shell 30. Some pores 40 in the surface extend downward to the surface shell to which the textured surface is applied other pores 50 are not as deep. Some of the pores interconnect so as to form a passageway or tunnel 60 that is bridged by encapsulated particles 70. Such passageways or tunnels can be created when encapsulated particles are built up on the surface so as to leave a void beneath the encapsulated particles. Some pores 80 are wider at or near the shell to which the particles are applied than they are at the exterior surface. Other pores 90 are narrower at or near the shell to which the particles are applied than they are at the exterior surface.

A textured surface can be applied to an article, e.g., an article having a formed of a polymer (e.g., an elastomeric polymer). When the article is formed of an elastomeric or polymeric material the surface to be textured is preferably somewhat tacky (e.g., the surface is uncured or partially cured silicone so that the particles at least lightly adhere to the surface to which they are applied). Particles, e.g., silicone particles, created as described below or by some other convenient method, are applied to the surface of the article. The particles can be applied over the entire outer surface of the article or just a portion of the outer surface of the article. The density of coverage by particles in a given region can be quite low or very high. For example, a given particle coated region may be 10%, 20%, 30%, 40%, 50%, 60%, 70%, 80%, 85%, 90%, 96%, 98% or 100% covered by particles. Within an applied layer of particles, the particles may be stacked one upon another or the particles are not stacked one upon another or not. Thus, a given layer of particles can be 1, 2, 3, 4 or more particles thick. Next, a polymer dispersion, e.g., a silicone dispersion, is applied to at least the particle covered portion of the article. The dispersion can be applied one or more times. A second layer of particles is then applied to the surface. This layer of particles can be applied to the same region as the previously applied layer of particles or it may only partially overlap the previously applied layer of particles. Again, this second layer may or may not include particles that are stacked one upon another. A polymer dispersion is applied to the second layer of particles. The application of particles and polymer dispersion can be repeated to result in two, three, four or more applications of each. The dispersion can optionally be partially polymerized or fully polymerized before the subsequent application of particles.

In the case of particles that are applied to a silicone surface that is partially cured, the silicone is optionally further cured or fully cured (polymerized) subsequent to the application of particles. For example, in the case of high temperature vulcanization (HTV) silicone, the device can be heated at 250-325° F. for 30 to 60 minutes. It is possible to apply the particles to uncured silicone. However, if solvent is present, for example if the particles are being applied to a silicone shell formed by dip casting, the solvent should be evaporated before the particles are applied so that the solvent does not permeate the particles. After the optional partial or full curing has been completed, non-adherent particles can be removed from the article by brushing or blowing. A silicone dispersion that includes silicone solids (e.g., HTV or RTV silicone) dissolved in a suitable solvent, e.g., xylene, toluene, hexane, methylene chloride, chloroform or tetrahydrofuran is used to coat the applied particles. The percent solids of the dispersion can be between 10 to 13% (e.g., 10-11.5%) or higher or lower (e.g., between 8% and 15% or between 6% and 17%). The dispersion can be applied to the particles by dipping, spraying, pouring or any other convenient means. For example, the dispersion can be applied by spraying as described in U.S. Ser. No. 10/918,277, filed Aug. 13, 2004. The excess solvent in the dispersion is allowed to volatilize and the article is optionally treated to partially or fully cure the silicone dispersion layer, e.g., in the case of HTV silicone, by heating to 250-325° F. for 30 to 60 minutes. The process of applying particles, optionally fully or partially curing, applying a silicone dispersion and optionally fully or partially curing again can be repeated. Thus, steps of applying particles, optionally fully or partially curing, applying a silicone dispersion and optionally fully or partially curing the applied silicone dispersion again can take place one, two, three, four, five or more times. Moreover, the average size of the silicone particles can vary from one application to another and can the density of the coverage. In some instances, the polymer dispersion is not even partially cured prior to the application of a subsequent layer of silicone particles. However, solvent is allowed to evaporate from the dispersion prior to the application of a subsequent layer or layers of silicone particles. Once the application of surface texture is complete, the device can be fully cured, e.g., by heating to 325° F. for 10 hours. Room temperature vulcanization (RTV) silicone can be used in the place of HTV silicone with the appropriate curing conditions.

Silicone particles can be created, for example, from fully cured silicone that is cryogenically ground to yield particles ranging in size from 20-1500 microns in diameter, e.g., 20-30, 20-40, 30-40, 30-50, 40-60, 40-70, 40-80, 50-100, 100-200, 200-300, 300-400, 400-500, 500-600, 600-700, 700-800, 800-900, 900-1000, 1000-1100, 1100-1200, 1200-1300, 1300-1400, 1400-1500 microns in diameter. For example, ¼ to ½ inch thick silicone sheets can be cryogenically ground to yield suitable particles. In some cases the particles are subsequently size selected, e.g., by sieving, such that the particles have a selected average size, e.g., 30-60 or 200-300 microns. In some cases the size selection is limited to removing very small particles and very large particles. In some cases at least 90% or at least 95%, 98% or 99% of the particles used in a given layer vary by no more than 100, 80, 60, 50, 40, 30, 20, 10 or 5 microns in diameter. In some cases the particles can be formed of partially cured silicone.

As noted above, the silicone particles can be applied several times. In some cases that average size of the silicone particles applied will vary. Thus, the particles applied in the first application of particles can have a first average size and the particles applied in the second application of particles can have a second average size. If there are is a third applications of particles, the particles in this third application can have a third average particle size. Thus, the particles used in each application can have a different average particle size. In some cases, several of the applications of particles can have the same or very similar average particle size. In some cases a given application of particles can include two different groups of particles, one having a first average particle size, e.g., 30-50 microns in diameter, and the other having a second, different average particle size, e.g., 100-150 microns in diameter.

The surface created on the shell can be microporous. There textured surface can include cavities, overhangs, and bridges above passageways. Thus, many of the cavities and interstices are large enough to permit cell ingrowth. However, because each layer of particles is enveloped in silicone, the surface is relatively smoothly modeled. The particles and polymer dispersion form an integral surface. Because the surface of the shell includes cavities, overhangs and passageways, upon implantation, tissue will grow into the cavities, beneath the overhangs and through the passageways. In this manner, the tissue is engaged with the implant and the implant is secured.

In some cases, either because the implant does not remain in the body for a sufficient period of time or due to other factors, for example, the size of the cavities and interstices, tissue will not become intimately engaged with the surface texture. However, the texture surface can nonetheless provide advantages such as reducing the type of scar formation associated with capsular contraction.

The cavities or pores can be 10, 20, 30, 40, 50, 60, 70, 80, 90, 100, 120, 140 or more microns deep depending on the size of the particles applied, the number of layers of particles applied and other factors. The diameter of the cavities or pores can be within the same range.

Example

A mammary prosthesis having a microporous surface texture can be prepared as follows. An elastomeric shell is formed by conventional dip-molding in an HTV silicone dispersion using an appropriately sized and shaped mandrel. After each dip, solvent is allowed to evaporate so that the new silicone layer is stabilized. The stabilization or solvent evaporation can be accelerated by heating (e.g., heating at 120° F. for 15 minutes). This process is repeated until a shell having the desired thickness is formed. After the last layer of silicone is applied, the shell can be partially or fully cured. While it is desirable to allow solvent to evaporate from the shell, it can be desirable to not cure the shell at all. The tackiness of an uncured silicone shell fosters adhesion of the solid particles. Once the shell has been formed, particles of fully cured HTV silicone having an average diameter of 100 microns are applied to the surface of the shell. Because the surface of the shell is tacky and because the particles have a static charge, the particles adhere readily. The particles can be applied at a density that allows almost complete coverage of the shell or partial coverage. Thus, the particles can be applied relatively densely so that there is little exposed shell or they can be applied relatively sparsely so that there is considerable exposed shell. In addition, as described in greater detail below, the particles can be applied to only a portion of the shell. The shell is heated (e.g., at 250-325° F. for 30 to 60 minutes) to partially cure or gel the silicone layer to which the particles are adhered. Particles that do not adhere to the shell can be removed by gently blowing air over the surface of the shell or by some other method. The shell is then dipped into a silicone dispersion (e.g., HTV silicone diluted 10% to 13% solids with xylene, toluene, tetrahydrofuran or some other suitable solvent) to apply a particle coating layer that envelops the applied particles. After excess silicone dispersion has been allowed to run off and the solvent has substantially or completely evaporated, the particle coating layer is partially cured or gelled (e.g., by heating to 250-325° F. for 30 to 60 minutes). The application of particles, curing, coating with silicone dispersion and curing is repeated two more times for a total of three application of particles and three applications of silicone dispersion. Finally, the shell is fully cured.

To create a complete mammary prosthesis, the now textured shell must be sealed. To do so, the shell is stripped from the mandrel. The opening in the posterior face of the shell is sealed using a patch comprising a cured layer of silicone sheeting and an uncured layer of silicone. The patch is shaped and sized to be somewhat larger than the opening in the posterior face of the shell and can include a filling valve. The patch is positioned inside the shell such that the uncured layer of the patch faces outward and the perimeter of the patch overlaps the edge of the shell surrounding the opening. The assembly is compressed either between hot platens at, e.g., 325° F. and 60 p.s.i. or platens at room temperature and 60 p.s.i. for about two to three minutes. The patched shell is then heated in an oven at 325° F. for about one half hour to cure fully.

In the case of a tissue expander, the shell can be provided with a remote or integral valve that permits periodic addition of filling liquid after the tissue expander has been implanted. For example, a needle can be used to pierce the skin and a self-sealing valve to add filling liquid to the device.

Figure 4:
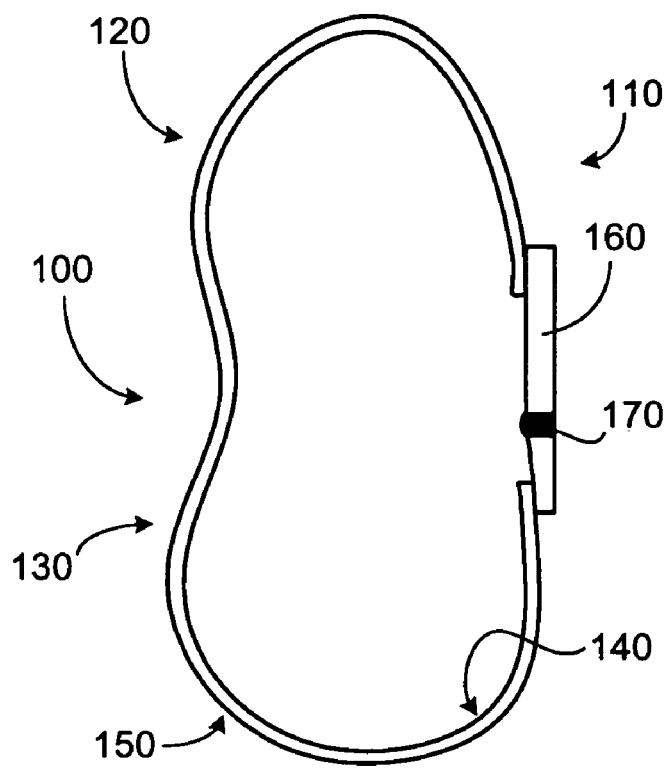
FIG. 4 is a schematic drawing of a cross-section of a mammary implant.

As noted above, the textured surface can be applied to all or only a portion of a device, e.g., a mammary prosthesis. For example, referring to FIG. 4, which shows a cross-section view of the shell 90 of a mammary prosthesis of the invention. The shell has an anterior face region 100, a posterior face region 110, an upper pole region 120 (i.e., the upper half of the shell when the prosthesis recipient is standing), a lower pole region 130 (i.e., the lower half of the shell when the prosthesis recipient is standing), an inner surface 140, an outer surface 150, a patch 160 and a filling port or valve 170 located on the posterior face region of the prosthesis. The posterior face region 110 of the shell is placed against the patient's chest wall when the prosthesis is implanted. It can be desirable to apply texture to the entire outer surface of the shell, only to the anterior face region, only to the posterior face region, only to the upper pole region (or the upper pole region of the anterior face), only the lower pole region (or the lower pole region of the anterior face) or to two or more regions or to the entire shell. It may also be desirable to apply more layers of particles to some regions of the shell than to others.

Other Embodiments

A soft tissue prosthesis can have any desired shape, e.g., the shell of the prosthesis can be circular, oval, or crescent shaped. The prosthesis can have a single lumen or multiple lumens. It can be formed of silicone, a laminate of various forms of silicone, silicone copolymers, polyurethane, and various other elastomers in various combinations. Various materials are described in U.S. Pat. Nos. 4,592,755 and 4,205,401.

The shell can be filled with a fluid or gel. In addition, an amount of solid material can be combined with the fluid or gel to adjust the density or compressibility of the filling.

The particles applied to create the textured surface can be formed of a non-polymeric material, e.g., they can be formed from any solid material.

The prosthesis of the invention can be provided as a kit with a shell and a means for filling the shell, e.g., a syringe. The kit can further include an adapter tube for connecting the syringe to the filling port of the shell.

A number of embodiments of the invention have been described. Nevertheless, it will be understood that various modifications may be made without departing from the spirit and scope of the invention.

The invention claimed is:

1. A method for creating a textured surface on a workpiece, the method comprising:
   a) providing a workpiece having a surface;
   b) applying particles of a solid polymeric material to at least a portion of the surface to create a particle covered portion of the surface;
   c) applying a polymer dispersion to at least the particle covered portion of the surface to create a coated surface;
   d) applying particles of a solid polymeric material to at least a portion of the coated surface in a non-uniform fashion to create the textured surface of the workpiece including cavities and interstices; and
   e) applying a polymer dispersion to at least the particle covered portion of the coated surface.

2. The method of claim 1 wherein steps d) and e) are repeated such that there are alternating multiple applications of particles of a solid polymeric material and multiple applications of polymer dispersion.

3. The method of claim 1 wherein the solid polymeric particles are silicone particles.

4. The method of claim 1 or 3 wherein the polymer dispersion is a silicone dispersion.

5. The method of claim 1 wherein the solid polymeric particles are silicone particles, the polymer dispersion is a silicone dispersion and wherein the silicone dispersion is at least partially cured after application but prior to any subsequent application of silicone particles.

6. The method of claim 5 wherein the workpiece is formed at least in part of silicone.

7. The method of claim 5 wherein the surface is uncured or partially cured silicone.

8. The method of claim 1, 5 or 7 wherein the workpiece is the shell of an implantable prosthesis.

9. The method of claim 8 wherein the prosthesis is a mammary prosthesis.

10. The method of claim 1 wherein the average size of the particles used in the first application of particles differs from the average size of the particles used in the second application of particles.

11. The method of claim 2 wherein the average size of the particles used in at least one of the multiple applications of particles differs from the average size of the particles used in at least one other of the multiple applications of particles.

12. The method of claim 11 wherein the average size of the particles in each of the multiple applications of particles differs in average size from the average size of the particles used in each of the other multiple applications of particles.

13. The method of claim 2 wherein steps d) and e) each occur at least two times.

14. The method of claim 2 wherein steps d) and e) each occur at least three times.

15. The method of claim 2 wherein steps d) and e) each occur at least four times.

16. The method of claim 2 wherein steps d) and e) each occur at least five times.

17. The method of claim 2 wherein steps d) and e) each occur at least six times.

18. The method of claim 1 wherein the polymer dispersion is applied by spraying.

19. The method of claim 1 wherein the polymer dispersion is applied by dipping.

20. The method of claim 1 wherein the particles of polymeric material are applied by spraying the particles.

21. The method of claim 1 wherein the particles of polymeric material are applied by dipping the workpiece into particles.

22. The method of claim 20 or 21 wherein the particles are suspended in a silicone dispersion and then applied.

23. The method of claim 3 wherein the silicone particles are formed of HTV silicone.

24. The method of claim 4 wherein the silicone dispersion is an HTV silicone dispersion.

25. The method of claim 4 wherein the silicone dispersion contains between 6% and 15% solids.

26. The method of claim 4 wherein the silicone dispersion contains between 8% and 13% solids.

27. The method of claim 4 wherein the silicone dispersion contains between 9% and 11% solids.

28. The method of claim 4 wherein the solvent in the silicone dispersion is xylene.

29. The method of claim 1, further comprising forming one or more of overhangs, tunnels or passageways in the surface.

30. The method of claim 1, further comprising forming a plurality of cavities in the surface, one or more of the cavities having a top and a base wider than the top.

31. A method for producing an implant shell having a textured surface, the method comprising:
  a) providing a implant shell formed of a polymeric material;
  b) applying particles of a solid polymeric material to at least a portion of at least one surface of the shell to create a particle covered portion of the surface;
  c) applying a polymer dispersion to at least the particle covered portion of the surface to create a coated surface;
  d) applying particles of a solid polymeric material to at least a portion of the coated surface in a non-uniform fashion to create the textured surface of the workpiece including cavities and interstices; and
  e) applying a polymer dispersion to at least the particle covered portion of the coated surface.

32. The method of claim 31 wherein steps d) and e) are repeated such that there are alternating multiple applications of particles of a solid polymeric material and multiple applications of polymer dispersion.

33. The method of claim 31 wherein the solid polymeric particles are silicone particles.

34. The method of claim 31 or 32 wherein the polymer dispersion is a silicone dispersion.

35. The method of claim 31 wherein the solid polymeric particles are silicone particles, the polymer dispersion is a silicone dispersion, and the silicone dispersion is at least partially cured before application of silicone particles.

36. The method of claim 31 wherein the implant is a mammary prosthesis.

37. The method of claim 32 wherein steps d) and e) each occur at least two times.

38. The method of claim 32 wherein steps d) and e) each occur at least three times.

39. The method of claim 31, further comprising forming one or more of overhangs, tunnels or passageways in the surface.

40. The method of claim 31, further comprising forming a plurality of cavities in the surface, one or more of the cavities having a top and a base wider than the top.

41. A method for producing a soft tissue prosthesis or tissue expander, the method comprising:
  a) providing a shell formed of a polymeric material;
  b) applying particles of a solid polymeric material to at least a portion of at least one surface of the shell to create a particle covered portion of the surface;
  c) applying a polymer dispersion to at least the particle covered portion of the surface to create a coated surface;
  d) applying particles of a solid polymeric material to at least a portion of the coated surface in a non-uniform fashion to create the textured surface of the workpiece including cavities and interstices;
  e) applying a polymer dispersion to at least the particle covered portion of the coated surface;
  f) sealing the shell and providing the shell with a filling port.

42. The method of claim 41, further comprising one or more of overhangs, tunnels or passageways in the surface.

43. The method of claim 41, further comprising forming a plurality of cavities in the surface, one or more of the cavities having a top and a base wider than the top.

44. The method of claim 41, further comprising permanently filling the shell with a fluid or a gel.

* * * * *

UNITED STATES PATENT AND TRADEMARK OFFICE
CERTIFICATE OF CORRECTION

| | | |
|---|---|---|
| PATENT NO. | : 7,645,475 B2 | Page 1 of 1 |
| APPLICATION NO. | : 11/071857 | |
| DATED | : January 12, 2010 | |
| INVENTOR(S) | : Prewett | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 727 days Delete the phrase "by 727 days" and insert -- by 1,129 days --

Signed and Sealed this

Fourth Day of May, 2010

David J. Kappos
*Director of the United States Patent and Trademark Office*